US00RE48038E

(19) United States
(12) Reissued Patent
van Dijk et al.

(10) Patent Number: US RE48,038 E
(45) Date of Reissued Patent: Jun. 9, 2020

(54) RECOGNITION OF IMPLANTABLE MEDICAL DEVICE

(71) Applicant: Cochlear Limited, Macquarie University, NSW (AU)

(72) Inventors: Bastiaan van Dijk, Mechelen (BE); Peter Gibson, South Coogee (AU)

(73) Assignee: Cochlear Limited, Macquarie University, NSW (AU)

(21) Appl. No.: 15/217,480

(22) Filed: Jul. 22, 2016

Related U.S. Patent Documents

Reissue of:
(64) Patent No.: 8,784,312
Issued: Jul. 22, 2014
Appl. No.: 12/279,055
PCT Filed: Feb. 9, 2007
PCT No.: PCT/AU2007/000142
§ 371 (c)(1),
(2) Date: Mar. 27, 2009
PCT Pub. No.: WO2007/090243
PCT Pub. Date: Aug. 16, 2007

(30) Foreign Application Priority Data

Feb. 10, 2006 (AU) ..... 2006900628

(51) Int. Cl.
*A61B 5/00* (2006.01)
*A61N 1/372* (2006.01)
(Continued)

(52) U.S. Cl.
CPC ..... *A61B 5/0002* (2013.01); *A61B 5/0031* (2013.01); *A61N 1/3727* (2013.01)

(58) Field of Classification Search
None
See application file for complete search history.

(56) References Cited

U.S. PATENT DOCUMENTS 4,532,930 A 8/1985 Crosby et al. ..... A61N 1/36036 607/57
4,776,322 A 10/1988 Hough et al.
(Continued)

FOREIGN PATENT DOCUMENTS

DE 19915846 8/2000
DE 19915846 C1 8/2000
(Continued)

OTHER PUBLICATIONS

International Search Report for PCT/AU01/00811 dated Sep. 10, 2001.
(Continued)

*Primary Examiner* — Glenn K Dawson
(74) *Attorney, Agent, or Firm* — Pilloff Passino & Cosenza LLP; Martin J. Cosenza

(57) ABSTRACT

Controlling the interaction between an external device and an implanted device, including a method of controlling interaction between an external device and an implanted device, the method including at least the steps of: establishing communications between the implanted device and the external device; the external device determining an identification of the implant and comparing the identification with identifications in a stored list; if the device matches one of said identifications, then using a corresponding set of operating parameters to interact with said implant; and otherwise, not interacting with said device.

54 Claims, 5 Drawing Sheets

(Amended)

(51) Int. Cl.

| | |
|---|---|
| ***A61B 5/02*** | (2006.01) |
| ***A61B 5/07*** | (2006.01) |

(56) References Cited

U.S. PATENT DOCUMENTS

| | | | | |
|---|---|---|---|---|
| 5,113,869 | A * | 5/1992 | Nappholz | A61B 5/0006 600/508 |
| 5,569,307 | A | 10/1996 | Schulman et al. | |
| 5,571,148 | A | 11/1996 | Loeb et al. | |
| 5,690,690 | A | 11/1997 | Nappholz et al. | |
| 5,701,348 | A * | 12/1997 | Shennib | H04R 25/456 381/322 |
| 5,800,473 | A | 9/1998 | Faisandier | |
| 5,817,137 | A | 10/1998 | Kaemmerer | |
| 5,891,180 | A | 4/1999 | Greeninger et al. | |
| 5,941,905 | A | 8/1999 | Single | A61N 1/36036 607/57 |
| 6,195,585 | B1 | 2/2001 | Karunasiri et al. | |
| 6,198,971 | B1 | 3/2001 | Leysieffer | A61N 1/36036 607/55 |
| 6,219,580 | B1 * | 4/2001 | Faltys et al. | 607/57 |
| 6,243,608 | B1 | 6/2001 | Pauly et al. | |
| 6,285,909 | B1 | 9/2001 | Sweeney et al. | |
| 6,308,099 | B1 | 10/2001 | Fox et al. | |
| 6,327,501 | B1 * | 12/2001 | Levine et al. | 607/27 |
| 6,443,891 | B1 * | 9/2002 | Grevious | 600/302 |
| 6,537,200 | B2 | 3/2003 | Leysieffer et al. | |
| 6,553,263 | B1 | 4/2003 | Meadows et al. | |
| 6,565,503 | B2 | 5/2003 | Leysieffer et al. | |
| 6,575,894 | B2 | 6/2003 | Leysieffer et al. | |
| 6,697,674 | B2 | 2/2004 | Leysieffer | |
| 6,738,670 | B1 | 5/2004 | Almendinger et al. | |
| 6,740,075 | B2 | 5/2004 | Lebel et al. | |
| 7,013,014 | B2 * | 3/2006 | Ach-Kowalewski | H04R 25/405 381/313 |
| 7,082,207 | B2 * | 7/2006 | Rapps | H04R 1/1075 381/330 |
| 7,174,214 | B2 * | 2/2007 | Seligman | H04R 25/556 607/57 |
| 7,346,397 | B2 | 3/2008 | Money et al. | A61N 1/36036 607/57 |
| 7,502,653 | B2 | 3/2009 | Daly | A61N 1/08 607/57 |
| 9,357,318 | B2 * | 5/2016 | Case | H04R 25/305 |
| 9,712,928 | B2 * | 7/2017 | Pedersen | H04R 25/558 |
| 2002/0045921 | A1 * | 4/2002 | Wolinsky | A61B 5/0028 607/61 |
| 2004/0024429 | A1 * | 2/2004 | Daly | A61N 1/08 607/59 |
| 2004/0176822 | A1 * | 9/2004 | Thompson et al. | A61N 1/37252 607/60 |
| 2005/0159791 | A1 * | 7/2005 | Daly | H04R 25/606 607/57 |
| 2005/0177205 | A1 * | 8/2005 | Kwon | A61N 1/36036 607/57 |
| 2006/0020304 | A1 * | 1/2006 | Torgerson et al. | 607/60 |
| 2006/0190059 | A1 * | 8/2006 | Griffith | A61N 1/37229 607/57 |
| 2007/0055321 | A1 * | 3/2007 | Gordon | A61N 1/37229 607/55 |
| 2007/0106345 | A1 * | 5/2007 | Seligman | H04R 25/556 607/57 |
| 2008/0039902 | A1 * | 2/2008 | Hartley | A61N 1/36036 607/57 |
| 2009/0292338 | A1 * | 11/2009 | Gordon | A61N 1/37229 607/57 |
| 2009/0306742 | A1 | 12/2009 | Van Dijk et al. | |
| 2010/0016922 | A1 | 1/2010 | Daly | |
| 2010/0024881 | A1 * | 2/2010 | Hacke | H01L 31/02244 136/256 |
| 2010/0249881 | A1 * | 9/2010 | Corndorf | A61N 1/37276 607/60 |
| 2011/0038499 | A1 * | 2/2011 | Chan | H04R 25/60 381/322 |
| 2011/0046698 | A1 * | 2/2011 | Kivi | H04W 76/19 607/60 |
| 2011/0082521 | A1 * | 4/2011 | Botros | A61B 5/04001 607/57 |
| 2011/0087306 | A1 * | 4/2011 | Goossen | A61N 1/3718 607/60 |
| 2015/0039052 | A1 * | 2/2015 | van Dijk | A61N 1/37252 607/57 |
| 2015/0289065 | A1 * | 10/2015 | Jensen | H04R 25/552 381/315 |
| 2016/0227332 | A1 * | 8/2016 | Pedersen | H04R 25/558 |
| 2016/0331952 | A1 * | 11/2016 | Faltys | A61N 1/37205 |

FOREIGN PATENT DOCUMENTS

| | | | |
|---|---|---|---|
| EP | 0730882 | | 9/1996 |
| EP | 0730882 | A2 | 9/1996 |
| WO | 00/72917 | A1 | 12/2000 |
| WO | WO 00/72917 | | 12/2000 |
| WO | 01/03622 | A1 | 1/2001 |
| WO | 01/06810 | A2 | 1/2001 |
| WO | WO 01/03622 | | 1/2001 |
| WO | WO 01/06810 | | 1/2001 |
| WO | 01/13991 | A1 | 3/2001 |
| WO | WO 01/13991 | | 3/2001 |
| WO | 03/003956 | A1 | 1/2003 |
| WO | 03/009207 | A1 | 1/2003 |
| WO | 03003956 | | 1/2003 |
| WO | 03009207 | | 1/2003 |

OTHER PUBLICATIONS

European Search Report for EP 01 95 1205.2 dated Mar. 31, 2005.
EPO Official Communication for EP 01 951 205.2 dated Feb. 2, 2006.
EPO Official Communication for EP 01 951 205.2 dated Sep. 14, 2006.
EPO Official Communication for EP 01 95 1205.2 dated Jan. 23, 2008.
Japanese Office Action for JP 2003-509972 dated Jun. 29, 2010.
International Search Report for PCT/AU2007/000142/ dated May 2, 2007.

* cited by examiner

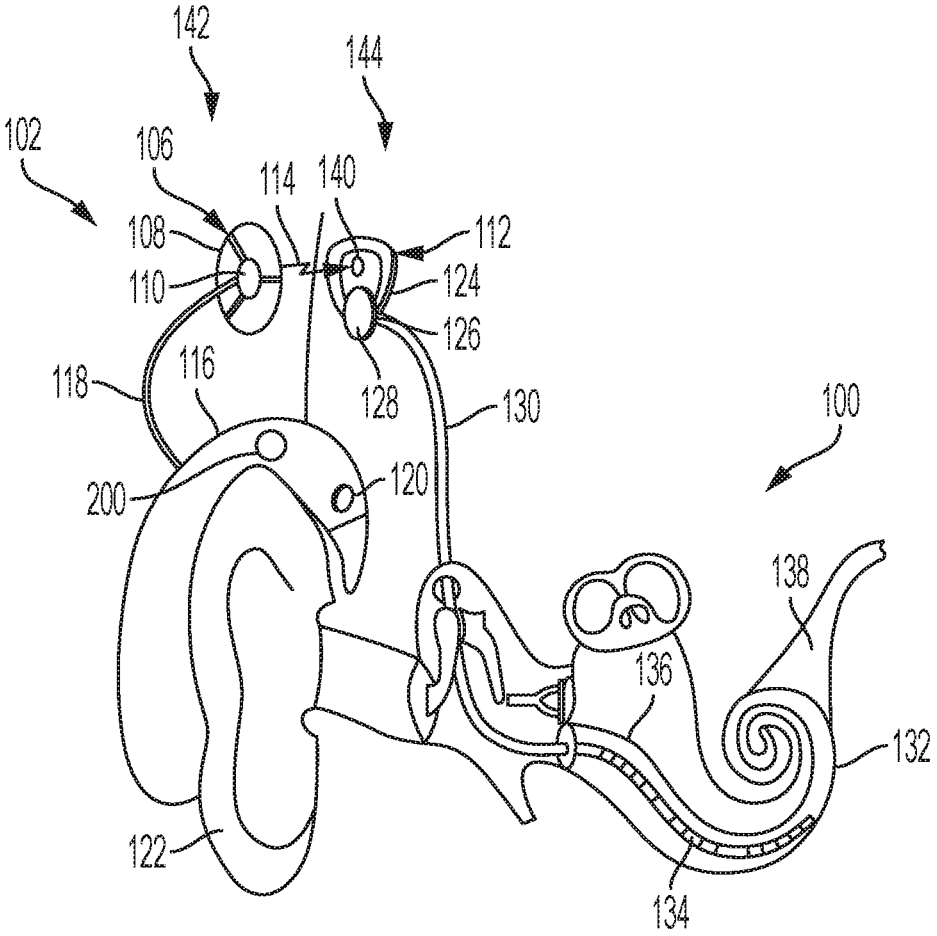
Figure 4
(Amended)

RECOGNITION OF IMPLANTABLE MEDICAL DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

*The present application is a reissue application of U.S. Pat. No. 8,784,312, issued Jul. 22, 2014, from application Ser. No. 12/279,055, filed Mar. 27, 2009.* The present application is a National Stage application of PCT/AU2007/000142 entitled "IMPLANT ID RECOGNITION", filed on Feb. 9, 2007, which claims priority from Australian Provisional Patent Application No. 2006900628, filed on Feb. 10, 2006, which are hereby incorporated by reference *in their entirety*.

BACKGROUND

1. Field of the Invention

The present invention relates to implantable medical devices, and more particularly, to recognition of implantable medical devices.

2. Related Art

Implantable hearing prostheses provide the benefit of hearing to individuals suffering from severe to profound sensorineural hearing loss. Sensorineural hearing loss is due to the absence or destruction of the hair cells in the cochlea which transduce acoustic signals into nerve impulses. An implantable hearing prosthesis essentially simulates the cochlear hair cells by delivering electrical stimulation to the auditory nerve fibers. This causes the brain to perceive a hearing sensation resembling the natural hearing sensation.

The present invention is particularly concerned with situations where a user, patient or recipient, "recipient" herein has an external processing device that communicates with an implanted device. For example, in a modern, conventional cochlear implant, an external speech processor transmits power and data to the implanted device via an inductive coil arrangement. The implanted device includes an electrode array to deliver the desired electrical stimuli to the cochlea of the recipient.

Once implanted, the implant system is typically adjusted to suit the specific needs of the recipient. As the dynamic range for electrical stimulation is relatively narrow and varies across recipients and electrodes, there is a need to individually tailor the characteristics of electrical stimulation for each recipient. This procedure, often referred to as "fitting," "programming," "mapping" ("mapping" herein) involves measuring and controlling the amount of electrical current delivered to the cochlea. Typically, a clinician, audiologist or other medical practitioner (generally and collectively referred to as "audiologist" herein) uses interactive software and computer hardware to create individualized programs, commands, data, settings, parameters, instructions, and/or other information (generally and collectively referred to as a "MAP" herein) that define the specific characteristics used to generate the electrical stimulation signals presented to the electrodes of the implanted electrode assembly. It is increasingly common for recipients to have a cochlear implant for each ear, which is commonly known as bilateral implantation. The advantages of bilateral implantation vary from recipient to recipient, and may include improved speech perception, and the ability to localize sounds. However, due to differences in the anatomy and physiology of recipients, and in the need to precisely place the electrode array, there will almost always be differences in the map between the left and right ears. The recipient will have two speech processor devices, each operating according to a different MAP. The speech processor devices are typically identical in appearance, and may inadvertently be swapped. This is a particular issue for very young and elderly recipients, as well as those with conditions such visual impairment. The use of the incorrect speech processor device will at best lead to reduced speech perception, as the incorrect MAP is applied, and potentially to pain for the recipient as excessive stimulation values are utilized for that ear.

SUMMARY

In a broad form, the present invention provides multiple sets of operating parameters (maps or the like) within each external device, each set being associated with an identified implant. Before the external device begins to transmit stimulation or other operational data to the implant, it determines the identity of the implant, and then uses the corresponding set.

According to one aspect, the present invention provides a method of controlling interaction between an external device and an implanted device, the method including at least the steps of:

establishing communications between the implanted device and the external device;

the external device determining an identification of the implant and comparing the identification with identifications in a stored list;

if the device matches one of said identifications, using a corresponding set of operating parameters to interact with said implant; and otherwise, not interacting with said device.

According to another aspect, the present invention provides an external device adapted to interact with an implanted device, the external device being adapted to detect an identification from an implanted device, determine if the identification corresponds to one of a plurality of identifications, and if the identification does correspond, utilise a stored set of operating parameters corresponding to said identification.

According to another aspect, the present invention provides an external hearing device adapted to interact with an implanted device, the external device being able to be operatively positioned to interact with either a left ear or right ear implanted device, said external device including sensor means operatively adapted to detect whether the external device is positioned to interact with the left ear or the right ear implanted device, and in response to said sensor utilise a stored set of operating parameters corresponding to the left ear or the right ear implanted device.

The present invention accordingly provides an arrangement whereby, for the bilateral implantee, it does not matter which SP is selected for which ear—both can store the map for each ear, and deliver the correct stimulation instructions for the respective implant. If the implant is not identified, the SP will not operate. The invention can be applied in any form of implanted device where multiple external devices may be inadvertently associated with the wrong implanted device.

The invention is also applicable to implanted devices where the external device may only be periodically connected, for example, a totally implantable auditory prosthesis.

BRIEF DESCRIPTION OF THE DRAWINGS

Embodiments of the present invention will now be described with reference to the accompanying figures, in which:

FIG. 4 illustrates the general operation of a cochlear implant system;

DETAILED DESCRIPTION

The present invention is capable of implementation in any desired type of implantable device which interacts with an external device. For example, the present invention may be used in conjunction with any acoustic or electrical auditory device, such as a middle ear implant, intracochlear array implant, brain stem implant, implanted acoustic device or any combination, for example combined electrical and acoustic stimulation. The external device may be continuously, intermittently or occasionally in communication with the implanted device. The present invention may also be used in non-auditory applications where a component is implanted and interacts with an external device. However, embodiments of the invention are described with reference to an embodiment in a cochlear implant system.

Figure 1:
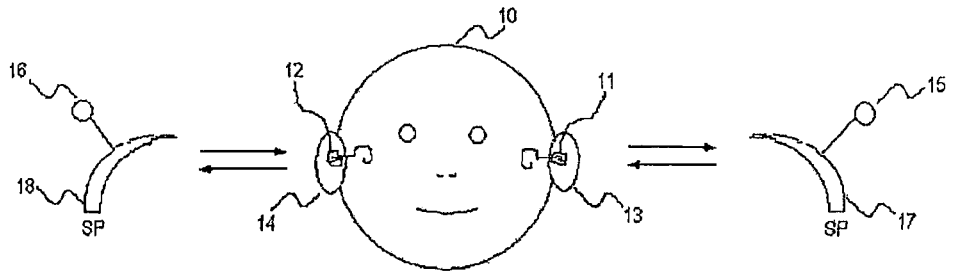
FIG. 1 illustrates schematically a bilateral implant situation.

FIG. 1 illustrates conceptually a recipient 10 having an intracochlear device 11, 12 implanted in each ear 13, 14, respectively. For each implant 11, 12, a corresponding external device 17, 18 is required. The external device incorporates one or more microphones, batteries, processor and the necessary software to process sound signals and transmit them via coils 15, 16 to the implanted device.

A more detailed description of typical external and implant devices of a cochlear implant is provided in FIG. 4. It is noted that such devices are in widespread commercial use, and well understood by those skilled in the art, so that only a general overview of their structure and operation will be provided. Moreover, various structural variations and alternatives exist, as will be well known to those skilled in the art.

FIG. 4 illustrates an overview of the components of one form of implantable hearing prosthesis, a cochlear implant. The external component of the cochlear implant, generally indicated as 142, includes a behind the ear (BTE) device 116, designed to sit behind the pinna 122. This houses the required electronics and software (not shown), and batteries to power the external component as well as transfer power to the implanted device 144. BTE device 116 is connected via a lead 118 to the antenna transmitter coil 106, which is generally disc shaped and includes housing 108 for the coil itself (not shown). A magnet 110 is provided to assist in correctly locating the antenna transmitter coil 106 relative to the implanted device, to optimize efficiency of power and data transfer.

The implanted component 144 includes receiver/stimulator unit 112 and electrode lead 130. Receiver stimulator unit 112 includes a sealed electronics package 128, and a coil 124 to receive the RF signals sent from transmitter coil 106. There may also be a back transmission mechanism, to transfer telemetry data to the external device 142. A magnet 140 provides assistance in alignment of the transmission coil 106. Electrode lead 130 passes stimuli to the electrodes 134 for delivery within the cochlea 132, so as to produce a neural response in auditory nerve 138.

In operation, the electronics within the BTE device 116 convert sound detected by microphone(s) 120 into a coded signal. The external antenna coil 106 transmits the coded signals, together with power, to the receiver/stimulator unit 112 via a radio frequency (RF) link.

Once implanted, the parameters for stimulation are typically adjusted to suit the specific needs of the recipient. As the dynamic range for electrical stimulation is relatively narrow and varies across recipients and electrodes, there is a need to individually tailor the characteristics of electrical stimulation for each recipient. Audiology measurements may be used to establish the useful range for each electrode, and such parameters can be stored within the recipient's BTE device 116 for continual use. As noted, this procedure is often referred to as "mapping" and is the term commonly given to the process of measuring and controlling the amount of electrical current delivered to each electrode, as well as selecting which electrodes to stimulate corresponding to the respective sound signal. Other operational issues which may differ between ears include the speech processing strategy or parameters of that strategy, when to switch between different strategies, and other functions and parameters. Different "MAPS" may be applied in different situations/environments such as home, car, classroom, theatre etc, so each external device may store many maps. It will be appreciated that the present invention is applicable to the selection of all such functions and parameters as may be customizable for each patient or implant according to the particular requirements and options of the implant and external device in question.

Importantly for the present invention, the MAP for each implant will differ due to variations in the patient's anatomy and physiology, and in the precise placement of the electrode array, there will almost always be differences in the MAP between the left and right ears.

Figure 2:
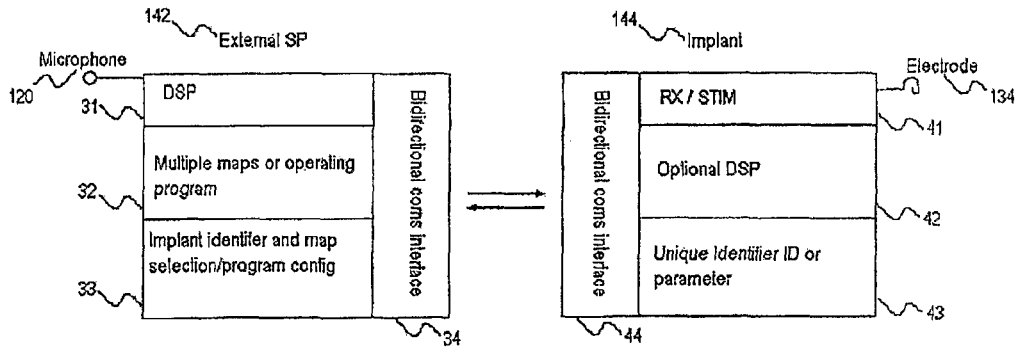
FIG. 2 is a conceptual block diagram of the operation of one implementation of the present invention.

FIG. 2 illustrates one implementation of the present invention. Microphone(s) 120 receives ambient sound signals which are then processed by a digital signal processor (DSP) 31. The signals are processed according to any one of the known speech processing strategies to produce a set of signals which are intended as the basis for stimulation. The signals are then converted into specific sets of stimuli for specific electrodes at specific times and for specific amplitudes. The set of MAPS (that is, the MAPS corresponding to different environments) for the appropriate implanted component 144 is required to perform this process. According to this implementation, multiple sets of MAPS are stored, each set of MAPS corresponding to a particular implant identifier. Embodiments of the implant identifier are described in further detail below. Module 33 selects the appropriate MAP, and other parameters as required, based on the implant ID identified by module 33. Once the stimuli have been determined, the appropriate coded signals are transmitted via the bidirectional communications interface 34 to interface 44 of implanted component 144. From the perspective of implanted component 144, it is not necessary to change the mode of operation. The receiver/stimulator 41 receives the signal, converts it to a set of stimuli, for example using an optional digital signal processor (DSP) 42, and sends the stimuli to electrodes 134.

Implanted component 144 may contain a module to provide the require ID signal. This may be any arrangement capable of providing an appropriate ID signal which is not shared with other implants. It is ideally unique, but need not be. One option would be to send a specific electrical signal after power up or after detection that the external device is in operation. This type of ID is used in some commercially available devices. Any alternative form of implant identification can be employed with the present invention.

One alternative would be to provide some form of specific automatic identification of which side of the recipient's head an external device, such as a BTE device, has been placed. This could be done by the use of a proximity or thermal sensor such as is shown as reference 200 on FIG. 4. In the thermal case, the sensor will operatively either be placed near adjacent the user's head, or facing away, with a substantial difference in heat. This allows the appropriate left or right map to be selected. However, this does not prevent the recipient from using a completely wrong device, as may occur in a classroom situation.

Another alternative would be to provide a source localization algorithm on the microphone in external device 17, 18. If the device is on the left ear, most sound will come from the right side and vice versa allowing determination of which ear the device has been placed and therefore allowing the appropriate selection of left or right map.

If no sensor is working and the implanted component is one that cannot transmit internal voltages, external device 17, 18 may still have MAPS for the left and right which the recipient 10 may select themselves, for example by pressing a selection button at start-up.

An approach suitable for use for an implant which has not been designed to produce a specific ID signal will be described with reference to FIGS. 5 and 6. The general approach is in principle applicable to any implant which is capable of sending the required parameters via a telemetry system to the external device. The principle of this approach is that each device has internal operating values that vary from device to device. The present example uses certain internal voltages which can be output using existing telemetry arrangements, and which as a statistical measure allow for accurate identification of particular implants. However, any suitable subset of internal parameters could be used as may be appropriate for a particular implant device.

Figure 5:
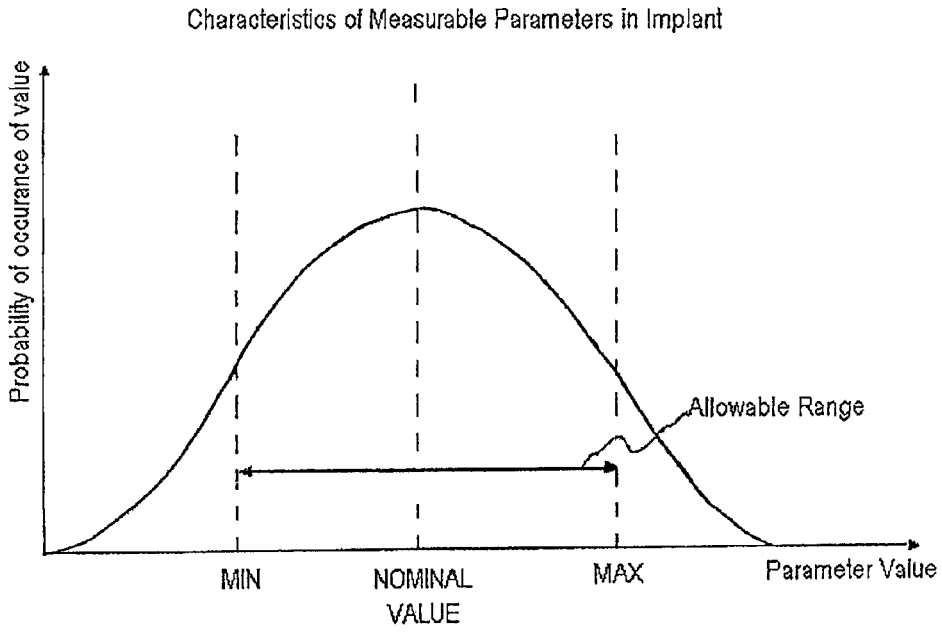
FIG. 5 illustrates the operation of another implementation of the identification system.

FIG. 5 illustrates the statistical basis used. In any real system, manufacturing variations result in various parameters having a normally distributed range of values about a nominal value. The parameters are required to fall within minimum and maximum ranges to be acceptable from a quality perspective. However, some of these values are relatively constant over time, and are a specific value of that parameter for the particular implant. When a number of these parameters are considered separately, then if there is a sufficient overall match, the implant can be sufficiently identified.

The choice of the suitable subset of parameters for use in device identification will depend on device design and the normal variance of the parameters. Most active implantable devices have a range of internal parameters that may be suitable, such as regulated supply voltages, reference voltages and programmable currents.

Figure 6A:
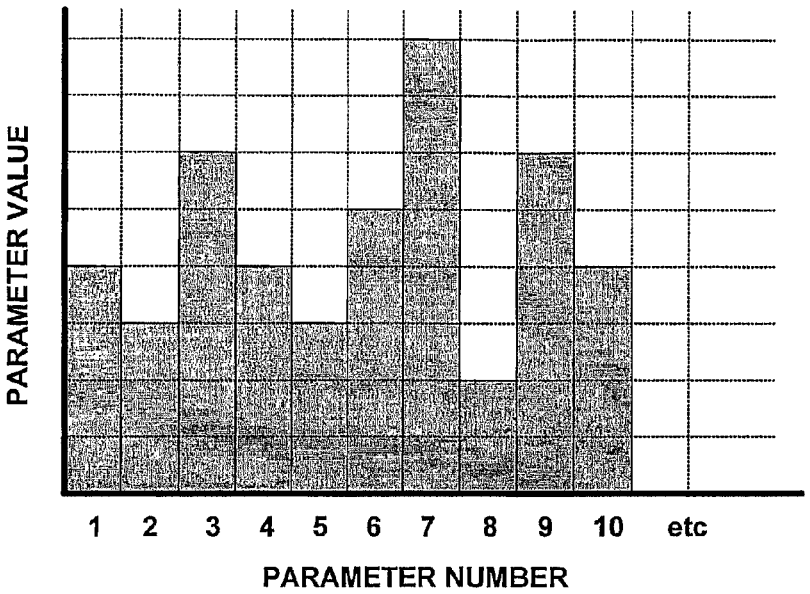
FIG. 6 is a graph illustrating how the characterisation of a predefined subset of parameters can be used to differentiate between two similar implants.
Figure 6B:
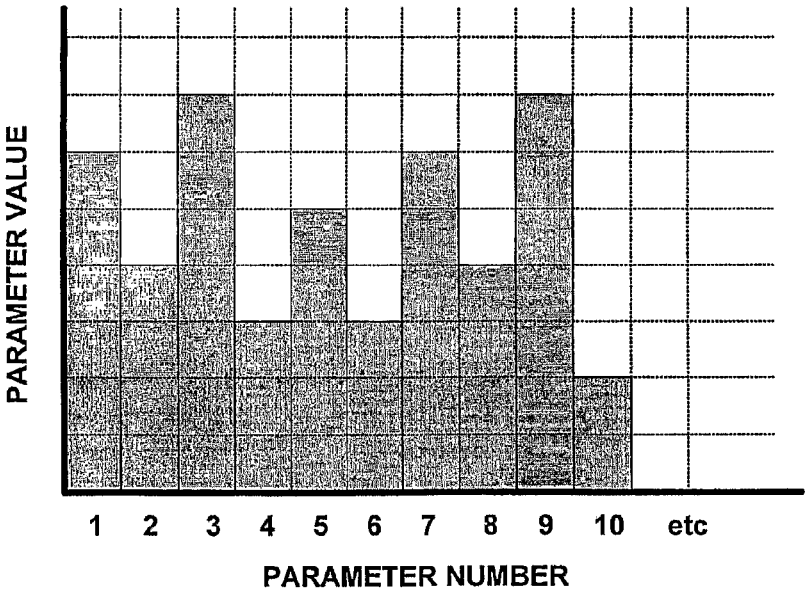

For example, referring to FIGS. 6A and 6B, the following parameters might be selected:

Parameter 1=Regulated analogue supply voltage (Vdda)

Parameter 2=Regulated digital supply voltage (Vddd)

Parameter 3=Reference voltage (Vref)

Parameter 4=Voltage measured across internal load for stimulus level A1

Parameter 5=Voltage measured across internal load for stimulus level A2, where the value of the internal load resistor and the two current levels A1 and A2 will vary between implants.

Parameters 6 to 10=Parameters 1 to 5 but measured using a different voltage measurement range. The gains of the different measurement ranges will vary between implants, for example due to the non-linearity of the voltage amplifier in each implant.

Alternatively, other measurements such as the physiological properties of the ear, eg some aspect of the neural response with the implant or the impedance of the electrodes in the cochlea, can be used as parameters for use in device identification.

FIGS. 6A and 6B show the value of various voltages, plotting the parameter value against the parameter. It can be seen that each implant has a specific signature which is different from other implants, so as to provide a specific identification of a particular implant. It is possible that another implant could have the set of parameter values, but this is sufficiently unlikely that that the practical risk of inadvertent connection may be disregarded.

One implant will now be described. For each implant (at the time of first surgery, or first fitting) the subset of parameters listed above is measured and stored as internal ID pattern. To improve the reliability of the measurement the parameters can be averaged, which also serves to minimize the statistical variance.

Every time the speech processor is placed on an implant the same subset of parameters is measured. The ID recognition test passes if and only if all of the parameters measured lie within, say T*sd of the value of that parameter in the internal ID pattern. The parameter T is a threshold that determines the trade-off between the sensitivity and specificity of the test: a large value of T means that we have a very low probability of wrongfully rejecting the correct implant (false negative rate), a small value of T means we have a low probability of wrongfully accepting the wrong implant (false positive rate). The parameter sd in the test criteria is the standard deviation of each parameter on repetitive measurement on the same implant, which is around 0.6 for the Freedom implant. Trials have indicated that T=3.25 provides acceptable false negative and false positive outcomes. It will be understood that for each type of implant, different parameters may be appropriate, and different values for T and standard deviation will need to be applied. The standard deviation may be different for different parameters.

It will be appreciated that this is a process which will differ for different external devices and a suitable set of identification parameters can be selected as has been described.

In practice, every time the speech processor is switched on stimulation should be halted until an implant is detected. Also, when a coil-off condition occurs for longer than 3 seconds, stimulation should halt until the implant is detected again. Before starting stimulation (at switch on, or after coil-off the test should pass first.

When an implant is (re)detected, the above mentioned parameters are measured using 50 averages. This dataset is labelled D(1) . . . D(n). The speech processor should check that for I=1 . . . n:

$$R(i)+T*sd<T(i)>R(i)-T*sd$$

When the test passes, stimulation can start. If the test fails, it is repeated to rule out statistical errors. When after five (5) tests, the test still fails the speech processor should refrain from stimulating and give a helper message on the LCD display of the implant.

It may be desirable in some applications that the user be able to overrule the error and start stimulation by a specific button press combination to manually select the correct operating program for the implant.

It will be understood that a different process may be used to implement the invention if desired, and that alternative processes are likely for different external devices.

Figure 3:
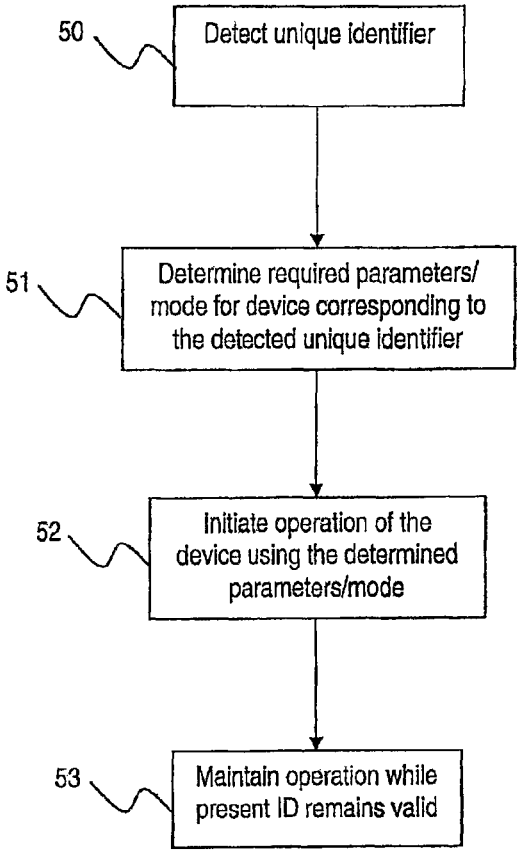
FIG. 3 is a flowchart illustrating the operation of the required software of one implementation.

FIG. 3 is a flow chart illustrating the process which can be employed in the BTE device 116 software. It is noted that it would be possible to perform the ID process primarily from the implant itself, however, in general it is preferred to minimise the complexity and processing load for the implanted device.

FIG. 3 shows the step 50 by which the identifier is detected. This will obviously differ depending upon the identifier used. Once the identifier is located, at step 51, the appropriate parameters and mode of operation will be selected, corresponding to the implant identified. It will be appreciated that the exact set of parameters will depend upon the type of implant, and apart from the map as such, may include other operating parameters, mode of stimulation, type of speech processing algorithm, and such other parameters as are desired.

It is preferred that the identification process occur as often as required to ensure safe operation. This may include, for example, at power on of the BTE device, or whenever communications between the implant and BTE are interrupted for more than some predetermined period, for example 3 seconds. In each case, the ID process should be completed before stimulation occurs.

Once the parameters are determined at step 51, operation of the device can be initiated. At step 53, operation can continue until conditions require the ID to be re-checked, as noted above.

It will be understood that the present invention may be applied to include more than two sets of operating parameters. For example, in a household where there are multiple implant users, all the SP devices could be loaded with the parameters for the implants of everyone in the house. This may be of particular benefit with small children. The present invention further provides flexibility for the user. If one SP device is not operating, for example due to low battery power, the remaining device can be used for the better ear.

Further features and advantages of the present invention may be found in International Application No. PCT/AU2007/000142 entitled "IMPLANT ID RECOGNITION", filed on Feb. 9, 2007, which claims priority from Australian Provisional Patent Application No. 2006900628, filed on Feb. 10, 2006, which are hereby incorporated by reference.

It will be appreciated that any other suitable identification process can be used in accordance with the present invention. Variations and additions can be readily added as will be apparent to those skilled in the art.

The invention claimed is:

1. An external hearing device adapted to interact with an [implanted] *implantable* internal device, the external device being able to be operatively positioned to interact with either a left ear or right ear [implanted] *implantable internal* device, said external device including a detector operatively adapted to detect whether the external device is positioned to interact with the left ear or the right ear *implantable* internal device, and *wherein the external hearing device is configured to,* in response to said detection, select and utilize a stored set of operating parameters corresponding to the left ear or the right ear *implantable* internal device to allow the external device to operate with the *implantable* internal device.

2. The external device according to claim 1, wherein the *implantable* internal device is a cochlear implant and the external device is a speech processor.

[3. The external device according to claim 1, wherein the detector includes one or more of a proximity sensor, a thermal sensor or a source localization algorithm stored in the external device.]

[4. The external device according to claim 1, wherein the operating parameters are selected from a group including one or more of an electrode map including stimulation levels, selection of electrodes to stimulate, speech processing strategy or algorithm, parameters of the speech processing strategy, or when to switch between different speech processing strategies.]

5. The external device according to claim 1, wherein the external device is configured to allow a user to manually select whether the set of operating parameters corresponding to the left ear or the right ear *implantable* internal device are utilized by the external device.

[6. The external device according to claim 1, further comprising a display, wherein the display is configured to display a message indicating at least the internal device that the external device is interacting with.]

7. The external device according to claim 1, wherein the detector is configured to determine at least one identifier of the left ear or the right ear *implantable* internal device.

8. The external device according to claim 7, wherein the identifier is a transmitted identification signal.

9. The external device according to claim 7, wherein the identifier is determined from a set of measured parameters related to one or more of either the *implantable* internal device [and] *or* physiological properties of [the left ear or the right ear internal device] *an ear of a recipient of the external device*.

10. The external device according to claim 7, wherein the identifier is an identification tag or device operating independently of the normal communication path between the left ear or the right ear *implantable* internal device and the external device.

11. The external device according to claim 7, wherein the [detector] *external device* is configured to compare the identifier of the left ear or right ear *implantable* internal device to a list of known identifiers to confirm that the *implantable* internal device is known.

12. The external device according to claim 11, wherein the [detector] *external device* is configured to select and utilize the set of operating parameters stored on the external device, the operating parameters corresponding to the *implantable* internal device, and enabling the external device to operate with the *implantable* internal device based on the comparison of the identifier of the left ear or right ear *implantable* internal device to the list of known identifiers.

[13. The external device according to claim 1, wherein the operating parameters are selected from a group including one or more of an electrode map including stimulation levels, selection of electrodes to stimulate, speech processing strategy or algorithm, parameters of the speech processing strategy, or when to switch between different speech processing strategies.]

14. The external device according to claim 1, wherein the external device [automatically] selects a [set of operating parameters] *map* to be utilized by the external device.

15. The external device according to claim 1, wherein the [detector] *external device* is configured to select and utilize the set of operating parameters from a plurality of operating parameter sets, wherein each operating parameter set of the plurality of operating parameter sets corresponds to a particular *implantable* internal device.

[16. The external device according to claim 1, wherein the external device is a behind-the-ear (BTE) external device.]

[17. The external device according to claim 11, wherein the detector is configured to periodically determine a new identifier and compare the new determined identifier to the list of known identifiers to confirm that the identifier is known.]

[18. The external device according to claim 7, wherein the detector is configured to terminate operation of the external device if the identifier is determined not to be known.]

*19. An external hearing device, the external device being able to be respectively operatively positioned at a first position to interact with a left ear implantable device and operatively positioned at a second position to interact with a right ear implantable device, said external device configured to detect whether the external device is positioned to interact with the left ear implantable device or the right ear implantable device, and in response to said detection, utilize a stored set of operating parameters corresponding to the left ear or the right ear implantable device, wherein*

*a plurality of sets of operating parameters are stored in the external hearing device, and the external hearing device is configured to select a respective set of operating parameters from the plurality of sets of operating parameters for the respective left ear implantable device and selects a respective set of operating parameters from the plurality of sets of operating parameters for the respective right ear implantable device.*

*20. The external hearing device of claim 19, wherein the left ear implantable device and the right ear implantable device are a stimulator/receiver unit of a cochlear implant and the external device is a cochlear implant speech processor.*

*21. The external hearing device of claim 19, wherein the external device configured to, upon a detection that the external device is positioned to interact with the left ear implantable device, utilize a first stored set of operating parameters from amongst the plurality of sets of operating parameters that are based on a MAP for the left ear, and to, upon a detection that the external device is positioned to interact with the right ear implantable device, utilize a second stored set of operating parameters from amongst the plurality of sets of operating parameters that are based on a MAP for the right ear, the MAP for the right ear being different than the MAP for the left ear.*

*22. A method for operating an external device with an implanted internal device, comprising:*

*establishing communications between the external device and the internal device;*

*determining, by the external device, at least one identifier of the internal device;*

*comparing, by the external device, the identifier of the internal device to a list of known identifiers to confirm that the internal device is known; and*

*selecting and utilizing, by the external device, a set of operating parameters stored on the external device, the operating parameters corresponding to the internal device, and enabling the external device to operate with the internal device.*

*23. The method of claim 22, wherein the internal device is a stimulator/receiver unit of a cochlear implant and the external device is a cochlear implant speech processor.*

*24. The method of claim 22, wherein the operating parameters include at least one of an electrode map including stimulation levels, which electrodes to stimulate, type of speech processing strategy or algorithm, parameters of the speech processing strategy, or when to switch between different speech processing strategies.*

*25. The method of claim 22, wherein the identifier is determined from a set of measured parameters related to one or more of either the internal device or physiological properties of an ear of a recipient of the external device.*

*26. The method of claim 22, wherein the internal device is an internal device of a hearing prosthesis, and the external device is an external device of the hearing prosthesis.*

*27. The method of claim 22, wherein the internal device is an internal device of a middle ear implant, and the external device is an external device of the middle ear implant.*

*28. The method of claim 22, wherein the internal device is an internal device of an implanted acoustic device, and the external device is an external device of the implanted acoustic device.*

*29. The method of claim 22, wherein the internal device is an internal device of an acoustic auditory device, and the external device is an external device of the acoustic auditory device.*

*30. The method of claim 22, wherein the internal device is an internal device of an electrical auditory device, and the external device is an external device of the electrical auditory device.*

*31. The method of claim 22, wherein the internal device is an internal device of a cochlear implant, and the external device is an external device of the cochlear implant.*

*32. The method of claim 22, wherein:*

*the action of utilizing, by the external device, the set of operating parameters includes using a different set of operating parameters that are different than a set of other currently stored operating parameters, the other currently stored operating parameters being also currently stored on the external device, and operating the internal device based on operating parameters selected during the action of selecting and utilizing, by the external device, a set of operating parameters; and*

*the method further includes subsequently to the action of selecting and utilizing:*

*establishing communications between the external device and a different internal device;*

*determining, by the external device, at least one identifier of the different internal device different than the determined at least one identifier of the internal device;*

*comparing, by the external device, the different identifier of the different internal device to the list of known identifiers to confirm that the different internal device is known; and*

*selecting and utilizing, by the external device, the set of other currently stored operating parameters stored on the external device, the other currently stored operating parameters corresponding to the different*

*internal device, and enabling the external device to operate with the different internal device.*

*33. The method of claim 32, further comprising the action of operating the different internal device based on the set of other currently stored operating parameters after enabling the external device to operate with the different internal device.*

*34. The method of claim 22, wherein the action of utilizing, by the external device, the set of operating parameters includes using a different set of operating parameters than a set previously utilized, and operating the internal device based on the set of operating parameters that was selected and utilized, by the external device without changing a mode of operation of the internal device.*

*35. The method of claim 22, wherein the action of selecting a set of operating parameters includes selecting a set of operating parameters from a plurality of sets of different operating parameters that are stored in the external device.*

*36. The method of claim 22, wherein the action of selecting a set of operating parameters includes selecting a set of operating parameters from a plurality of sets of different operating parameters that are stored in the external device, wherein at least one of the sets of different operating parameters of the plurality of sets of different operating parameters corresponds to a set of operating parameters for a second implanted device, which at least one of the sets of different operating parameters is not selected and not utilized based on the action of comparing the identifier of the internal device.*

*37. The method of claim 22, wherein:*

*the actions of establishing communications, determining at least one identifier, comparing the identifier and selecting and utilizing the set of operating parameters are executed while the external device is located against the head of a recipient.*

*38. The method of claim 22, wherein the action of establishing communications between the external device and the internal device is executed via an antenna transmitter coil that is located proximate a head of a recipient outside the skin of the recipient and a receiver coil that is located inside the head of the recipient.*

*39. The method of claim 22, wherein the external device includes a first component held against skin of a recipient via magnetic interaction with an implanted ferromagnetic material that is part of the implanted internal device, wherein the action of establishing communications between the external device and the internal device is executed using the first component.*

*40. The method of claim 22, wherein the method of operating is a method of controlling operation of the implanted device with the external device.*

*41. The method of claim 22, wherein the action of establishing communications between the external device and the internal device is executed via a transmitter component that is located proximate a head of a recipient outside the skin of the recipient and a receiver component that is located inside the head of the recipient.*

*42. The method of claim 22, wherein the external device includes a first component held against skin of a recipient via magnetic interaction with an implanted magnet that is part of the implanted internal device, wherein the action of establishing communications between the external device and the internal device is executed using the first component.*

*43. An external device adapted to interact with an implantable internal device, the implantable internal device having at least one identifier, and the external device having a stored set of operating parameters; the external device configured to detect the identifier from the implantable internal device, determine if the identifier corresponds to one of a plurality of identifiers, and if the identifier does correspond, select and utilize a stored set of operating parameters corresponding to the identifier that corresponds to one of the plurality of identifiers to allow the external device to operate with the implantable internal device.*

*44. The external device of claim 43, wherein the implantable internal device is a hearing prosthesis implant and the external device is a speech processor.*

*45. The external device of claim 43, wherein the stored set of operating parameters include at least one of an electrode map including stimulation levels, selection of electrodes to stimulate, speech processing strategy or algorithm, parameters of the speech processing strategy, or when to switch between different speech processing strategies.*

*46. The external device of claim 43, wherein the implantable internal device is an internal device of a hearing prosthesis, and the external device is an external device of the hearing prosthesis.*

*47. The external device of claim 43, wherein the implantable internal device is an internal device of a middle ear implant, and the external device is an external device of the middle ear implant.*

*48. The external device of claim 43, wherein the implantable internal device is an internal device of an implanted acoustic device, and the external device is an external device of the implanted acoustic device.*

*49. The external device of claim 43, wherein the implantable internal device is an internal device of an acoustic auditory device, and the external device is an external device of the acoustic auditory device.*

*50. The external device of claim 43, wherein the implantable internal device is an internal device of an electrical auditory device, and the external device is an external device of the electrical auditory device.*

*51. The external device of claim 43, wherein the implantable internal device is an internal device of a cochlear implant, and the external device is an external device of the cochlear implant.*

*52. The external device of claim 43, wherein:*

*the stored set of operating parameters is based on a MAP for an implantable electrode array of the implantable internal device customized for the recipient of the implantable internal device.*

*53. The external device of claim 43, wherein:*

*the external device includes a plurality of different stored sets of operating parameters, wherein respective different stored sets of operating parameters of the plurality of different stored sets of operating parameters are respectively based on respective different MAPs for different implantable electrode arrays of the implantable internal device.*

*54. The external device of claim 43, wherein:*

*the external device is configured to be worn directly against the head of a recipient.*

*55. The external device of claim 43, wherein:*

*the external device is configured to be worn directly against the body of a recipient, and*

*the external device is configured to execute the following actions:*

*interact with the implantable internal device,*

*detect the identifier from the implantable internal device,*

*determine if the identifier corresponds to one of a plurality of identifiers, and if the identifier does*

*correspond, select and utilize a stored set of operating parameters corresponding to said corresponding identifier to allow the external device to operate with the implantable internal device.*

*56. The external device of claim 43, wherein:*

*the implantable internal device is a stimulator/receiver unit of a cochlear implant and the external device is a cochlear implant speech processor.*

*57. The external device of claim 43, wherein:*

*the external device includes a component configured to be worn directly against the head of a recipient, the component including an antenna transmitter coil, the external device being in signal communication with a speech processor of the external device.*

*58. The external device of claim 43, wherein:*

*the external device is a Behind-The-Ear (BTE) device.*

*59. The external device of claim 43, wherein the external device is configured to operate with at least two separate implantable internal devices, during separate temporal periods, that have respective different identifiers.*

*60. The external device of claim 43, wherein the external device is configured to*

*determine if the identifier corresponds to one of at least two different implantable internal device identifiers, and operate a first way if it is determined that the identifier corresponds to one of the at least two different internal device identifiers, and operate a second way different from the first way if it is determined that the identifier corresponds to another of the at least two different internal device identifiers.*

*61. The external device of claim 43, wherein the external device is configured to*

*interact with and operate with respective different implantable internal devices that have respective different identifiers during respective different temporal periods by selecting and using respective stored sets of operating parameters, stored in the external device, corresponding to the respective identifiers.*

* * * * *